United States Patent [19]

Feygin

[11] Patent Number: 5,957,167
[45] Date of Patent: Sep. 28, 1999

[54] ARTICLE FOR DISPENSING SMALL VOLUMES OF LIQUID

[75] Inventor: Ilya Feygin, Mountainside, N.J.

[73] Assignee: Pharmacopeia, Inc., Princeton, N.J.

[21] Appl. No.: 08/993,106

[22] Filed: Dec. 18, 1997

[51] Int. Cl.⁶ .................................................. G01F 11/00
[52] U.S. Cl. ............................... 141/31; 141/1; 141/130; 141/284; 422/100; 73/864.02; 73/864.72
[58] Field of Search ................................ 141/1, 31, 130, 141/284; 73/864.02, 864.72; 422/100

[56] References Cited

U.S. PATENT DOCUMENTS

| | | | |
|---|---|---|---|
| 3,358,496 | 12/1967 | Farmer | 73/864.72 |
| 3,536,449 | 10/1970 | Astle | 73/864.72 |
| 3,568,735 | 3/1971 | Lancaster | 141/238 |
| 4,116,637 | 9/1978 | Kitahara | 73/864.72 |
| 4,260,467 | 4/1981 | Smith et al. | 204/413 |
| 4,309,912 | 1/1982 | Smith | 73/864.72 |
| 4,731,335 | 3/1988 | Brigati | 73/864.72 |
| 4,939,410 | 7/1990 | Nagy et al. | 313/231.01 |
| 5,226,462 | 7/1993 | Carl | 141/1 |
| 5,230,864 | 7/1993 | Columbus | 422/100 |
| 5,334,353 | 8/1994 | Blattner | 422/100 |
| 5,456,294 | 10/1995 | Tsao et al. | 141/1 |
| 5,460,782 | 10/1995 | Coleman et al. | 422/100 |
| 5,578,178 | 11/1996 | Nuzzio | 204/413 |
| 5,763,278 | 6/1998 | Sickinger et al. | 422/100 |
| 5,770,151 | 6/1998 | Roach et al. | 73/864.02 |
| 5,807,735 | 9/1998 | Brown et al. | 422/50 |

FOREIGN PATENT DOCUMENTS

| | | | |
|---|---|---|---|
| 627480 | 9/1961 | Canada | 239/220 |

OTHER PUBLICATIONS

Product information on "Replicators"and "Replicator Accessories" obtained Nov. 7, 1997 from V&P Scientific, Inc. web site at WWW.vp–scientific.com.

*Primary Examiner*—J. Casimer Jacyna
*Attorney, Agent, or Firm*—DeMont & Breyer

[57] ABSTRACT

A method for handling and dispensing small volumes of liquid, and apparatus for carrying out the method, are disclosed. A small volume of liquid, which is retained within a fluid-dispensing member, is dispensed therefrom by accelerating, and then abruptly decelerating, the member. The abrupt deceleration causes the retained liquid to discharge. The discharged liquid may be directed toward a receiver. A micro volume liquid dispenser for practicing the method includes a plurality of fluid-dispensing members configured for aspiring and retaining a small liquid volume via capillary action. The dispenser further includes an actuator for moving/accelerating the fluid-dispensing members and for stopping/abruptly decelerating the fluid-dispensing members.

26 Claims, 3 Drawing Sheets

ARTICLE FOR DISPENSING SMALL VOLUMES OF LIQUID

FIELD OF THE INVENTION

The present invention relates to an article and method for handling and dispensing small volumes of liquid.

BACKGROUND OF THE INVENTION

During the course of research and development, production and other technological activities in a variety of different fields, a need arises to handle, transfer and dispense very small volumes of liquid. "Micro volume" liquid handling and dispensing systems, suitable for handling liquid volumes on the order of a microliter, have been developed to satisfy such a need.

Micro volume liquid dispensing systems are categorizable, generally, into one of two groups based on the way in which they dispense their charge of liquid. In a first group of such micro volume delivery systems, a portion of the dispensable liquid, while still in its dispenser, is brought into contact with a receiving body ("the receiver"). Based on a difference in surface tension between liquid in the dispenser and liquid contacting the receiver, the liquid is drawn out of the dispenser and into the receiver. Such systems may be categorized as requiring "touch-off." Exemplary touch-off-based micro volume dispensing devices include capillary tubes, wettable pegs or pins and syringes using "drop touch-off," among others. Dispensing devices included within the first group tend to be mechanically simple and inexpensive. Unfortunately, it may be undesirable or impractical to bring the dispenser close enough to the receiver to effect liquid contact. In particular, in the medical, chemical and biological arts, such close contact may cause undesirable carryover or cross contamination wherein a substance in the receiver is drawn into or onto the dispenser. Moreover, cleaning capillary tubes and syringes, such as may be required between each touch-off due to a change in the dispensed liquid or to avoid cross contamination, can be problematic.

In a second group of micro volume liquid dispensing systems, which may be categorized as "non touch-off," the dispensable liquid is forcibly ejected from the dispenser. Exemplary devices utilizing such an ejection method include piezo or thermally-actuated liquid ejectors as are often used in print heads, solenoid modulators of pressurized liquid flows and micrometering pumps. Such devices avoid the aforementioned drawback associated with touch-off; however, they suffer from other drawbacks. In particular, both piezo and thermally actuated liquid ejectors are limited to use with extremely small volumes of liquid, and typically require very clean and specially-developed fluids. Such restrictions limit the utility of liquid ejectors in chemical, biochemical and related arts. Pumps and flow modulators are usually very expensive, bulky, slow, have limited reliability and are often incompatible with biochemical or chemical reagents, as well.

Moreover, most of the conventional micro volume liquid dispensers mentioned above are not readily adaptable for use in systems requiring multiple dispensing ports. As such, their use is precluded or substantially curtailed in high throughput chemistry and screening applications. Thus, there is a need for a simple and reliable system suitable for transferring small volumes of a variety of liquids and possessing multi-point dispensing capability.

SUMMARY OF THE INVENTION

A method for handling and dispensing small volumes of liquid, and apparatus for carrying out the method, are disclosed. In accordance with the invention, a small volume of liquid, which is retained within a carrier, is dispensed therefrom by accelerating, and then abruptly decelerating, the carrier. The dispensed liquid is directed toward a receiver.

The method is carried out using a micro volume liquid dispenser that includes, as a liquid carrier, a plurality of fluid-dispensing members. Each fluid-dispensing member comprises two opposed surfaces in spaced relation to one another and suitably configured for aspiring and holding a small volume of liquid via capillary action. Each fluid-dispensing member retains and delivers a liquid volume within the range of about 0.5 to about 5 microliters. The present micro volume liquid dispenser further includes an actuator for moving/accelerating the fluid-dispensing members and for stopping/abruptly decelerating the fluid-dispensing members. The actuator can use a biasing member, such as a spring, for accelerating the fluid-dispensing members, and a "stop" for abruptly decelerating the fluid-dispensing members. Alternatively, the actuator can utilize more sophisticated pneumatic, hydraulic or electrodynamic systems. As noted above, abruptly decelerating moving fluid-dispensing members causes retained liquid to issue therefrom. Such dispensed liquid can be directed toward, and received by, an intended receiver.

Unlike conventional capillary tubes, the "open" capillary design of the present fluid-dispensing members advantageously allows for efficient cleaning, as is desirable between transfers of different liquids. Moreover, the present micro volume liquid dispenser is a "non touch-off" type of device, avoiding potentially undesirable contact with the receiver. Unlike most conventional non touch-off based devices, the present dispenser is inexpensive, reliable, fast and compatible with a wide range of biochemical or chemical reagents of varying purities.

BRIEF DESCRIPTION OF THE DRAWINGS

Further features of the invention will become more apparent from the following detailed description of specific embodiments thereof when read in conjunction with the accompanying Figures in which.

DETAILED DESCRIPTION OF THE INVENTION

Figure 1:
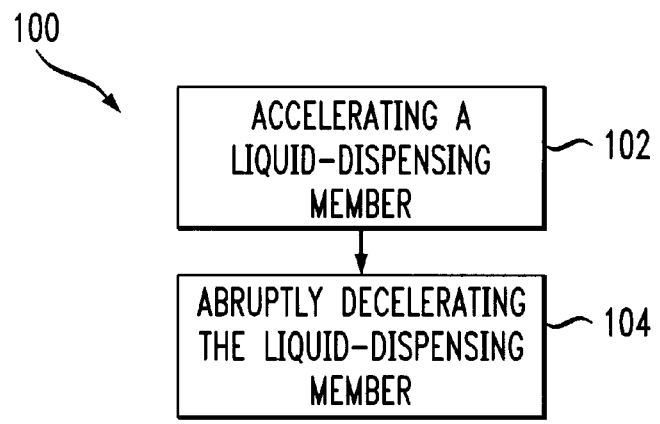
FIG. 1 is a flow diagram of a method in accordance with the present invention.

A method 100 in accordance with the present invention is illustrated by flow diagram in FIG. 1. According to the method, a small volume of liquid is delivered to a receiver by accelerating a liquid-containing carrier, hereinafter referred to as a "fluid-dispensing member," along a first direction, as indicated in operation block 102, and then abruptly decelerating it, as per operation block 104. Abrupt deceleration of the fluid-dispensing member causes liquid retained therein to issue therefrom substantially along the first direction. A receiver is positioned near to the fluid-dispensing member to receive the dispensed liquid.

Figure 2:
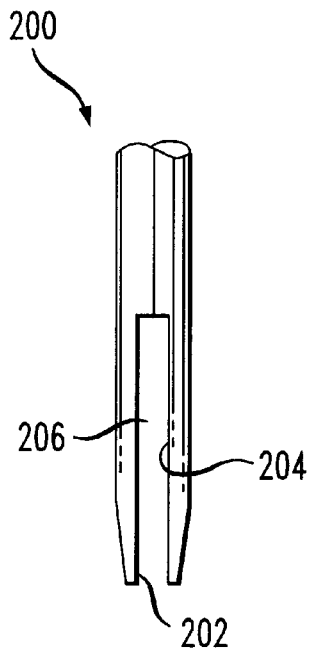
FIG. 2 shows a first exemplary embodiment of a fluid-dispensing member.

In a further aspect of the present invention, the present method 100 for liquid delivery is carried out using a micro volume liquid dispenser described in this specification. Such a dispenser incorporates a plurality of the aforementioned fluid-dispensing members, each capable of delivering a liquid volume in the range of about 0.5 to about 5 microliters. Preferably, the liquid carrier is configured to receive and retain its liquid charge via capillary action. A fluid-dispensing member 200 for use in conjunction with the present invention is shown in FIG. 2.

Fluid-dispensing member 200 has two opposed surfaces 202, 204 that are separated by gap 206. In one embodiment, surfaces 202 and 204 are concave. Such concave opposed surfaces can be obtained, for example, by forming a slit in a capillary tube. In a second embodiment, surfaces 202 and 204 are substantially flat. Such flat opposed surfaces can be obtained, for example, forming a slit in a solid rod. The dimensions of gap 206 and surfaces 202, 204 are suitably selected to allow aspiration and retention of a chosen liquid via a capillary effect.

It is expected that differences among liquids (e.g., surface tension, etc.) will not substantially affect the physical configuration (e.g., gap sizing, surface dimensions, etc.) of fluid dispensing member 200, such that a single micro volume liquid dispenser according to the invention will be suitable for use with a variety of liquids. Gap 206 having a dimension in the range of about 1 to about 1.5 millimeters (mm), and opposed surfaces 202, 204 having a width of about 1 mm or more are expected to be satisfactory for use with a wide range of liquids. Surfaces 202, 204 can be plastic or glass, and, may be suitably coated with noble metals, teflon$^{TM}$ or the like.

Figure 3:
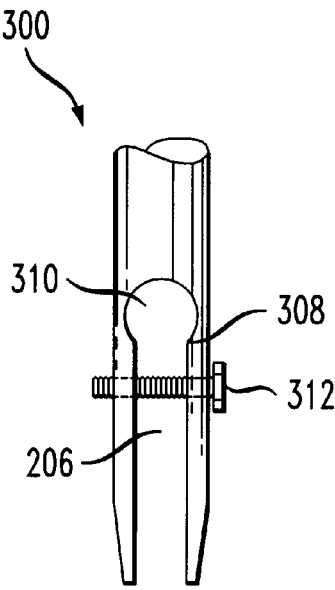
FIG. 3 shows second exemplary embodiment of a fluid-dispensing member.

In some embodiments, such as the exemplary embodiment shown in FIG. 3, the size of gap 206 is adjustable. Such adjustability is provided by gap adjuster 312. A simple, easily implemented embodiment of gap adjuster 312 is a "tightening screw," as is depicted in FIG. 3.

In some embodiments, a discontinuity, disruption or other change in the gap/surfaces is utilized to terminate the capillary action of opposed surfaces 202, 204, thereby allowing a fluid-dispensing member 300 to aspire a predetermined and repeatable volume of liquid. In one exemplary embodiment, shown in FIG. 3, the discontinuity is a "widening" 310 that is located at inner terminus 308 of gap 206.

Figure 4:
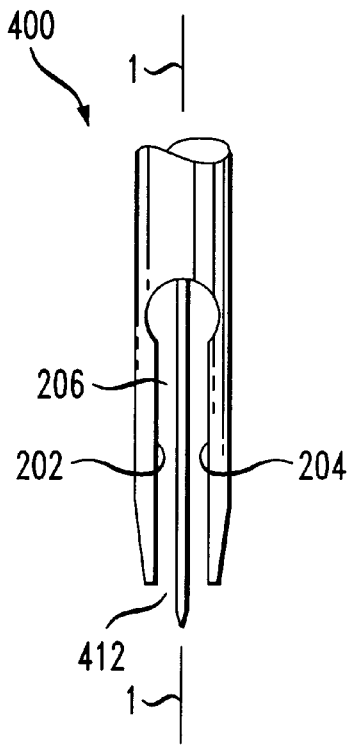
FIG. 4 shows a third exemplary embodiment of a fluid-dispensing member.

Differences in dimensions between surfaces 202, 204, or between surface characteristics of surfaces 202, 204 resulting in local variations in surface tension may cause a deviation in the course of liquid issuing from a fluid-dispensing member. To reduce or eliminate any such deviation for those or other reasons, the fluid-dispensing member includes, in some embodiments, liquid director 412, such as is shown in FIG. 4. Liquid director 412, configured as a "needle-like" structure in the embodiment shown in FIG. 4, is disposed within gap 206 along a centrally-located long axis 1—1 of fluid-dispensing member 400. Liquid director 412 extends beyond opposed surfaces 202, 204 in the aforementioned axial direction.

During the dispensing process, the dispensable volume of liquid slides along liquid director 412 forming a symmetrical droplet due to its surface tension. The liquid, after disassociating from liquid director 412, maintains a substantially straight-line course out of the dispenser along axis 1—1. It should be understood that liquid directors having other physical configurations, as may be devised by those skilled in the art, and operable to direct a small volume of liquid along a predetermined direction, may suitably be used in place of the aforedescribed structure.

Figure 5:
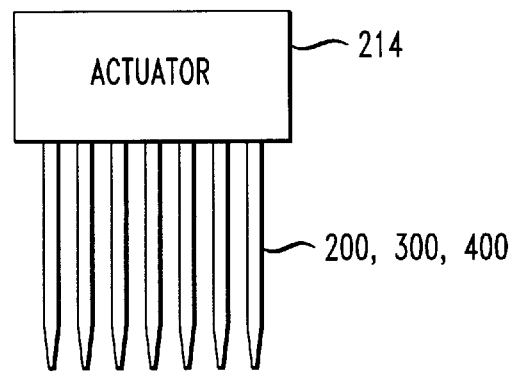
FIG. 5 shows a conceptual illustration of a micro volume liquid dispenser suitable for carrying out the present method.

The micro volume liquid dispenser further includes actuator 214 for moving/accelerating fluid-dispensing members 200, 300 or 400, and for stopping/decelerating the fluid-dispensing members, as shown conceptually in FIG. 5. As described further below, actuator 214 can utilize any of a number of different types of forces for accelerating and decelerating the fluid-dispensing members. Additionally, different instrumentalities may be used for accelerating and decelerating the fluid-dispensing members, or, alternatively, a single instrumentality can be used for both operations.

Figure 6:
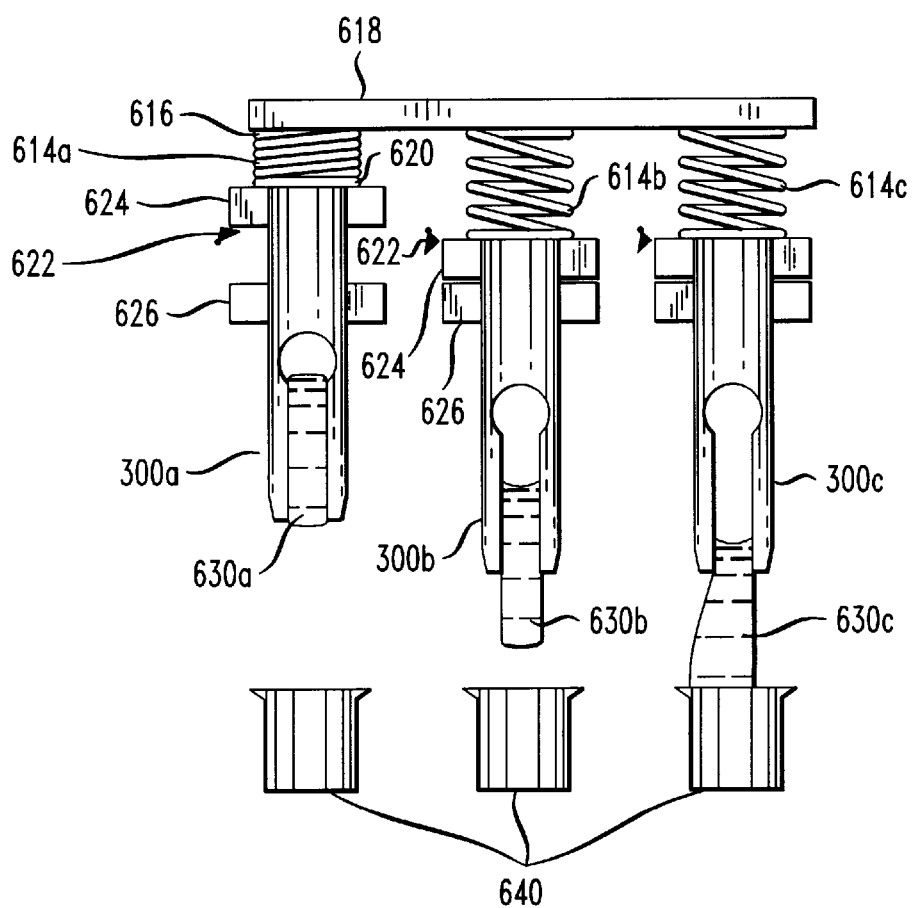
FIG. 6 shows a first exemplary embodiment of the micro volume liquid dispenser of FIG. 5.

An illustrative embodiment of micro volume liquid dispenser 600 in accordance with the present invention is depicted in FIG. 6. In the embodiment shown in FIG. 6, actuator 214 comprises a biasing member configured as helical spring 614a–614c, movable stop member 624 and fixed stop member 626.

Each helical spring 614a–614c is attached, at a first end 616, to rigid base 618, and, at a second end 620, one each to respective fluid-dispensing members 300a –300c. To develop energy for accelerating a fluid-dispensing member, such as fluid-dispensing member 300a, spring 614a is placed in a compressive state, as shown in FIG. 6. Spring 614a is maintained in such a compressed state using, for example, latch 622. To dispense liquid 630a, latch 622 is released, allowing spring 614a to expand and release its stored energy. As a result, attached fluid-dispensing member 300a is accelerated in the direction of expansion.

Before an expanding spring, such as spring 614b, is restored to a fully uncompressed state, movable stop member 624 depending from fluid-dispensing member 300b contacts fixed stop member 626, halting expansion of the spring and abruptly decelerating the fluid-dispensing member. Abruptly decelerating a fluid-dispensing member, such as fluid-dispensing members 300b, 300c, causes liquid 630b, 630c retained therein to discharge. The liquid can be discharged into appropriately positioned receivers 640.

It will be appreciated that a wide variety of configurations suitable for accelerating and abruptly decelerating the fluid-dispensing members can be used in conjunction with the present invention. For example, with reference to FIG. 7, rather than attaching a biasing member to each fluid-dispensing member 300a–300c, the fluid-dispensing members could be attached directly to rigid movable base 718. One or more biasing members, such as helical springs 714a, 714b, each one of which is capable of storing and releasing more energy than any one of springs 614a–614c, are placed between rigid movable base 718 and a second rigid non-moving surface 720. Latches or the like, not shown, are operable to compress helical springs 714a, 714b.

Figure 7:
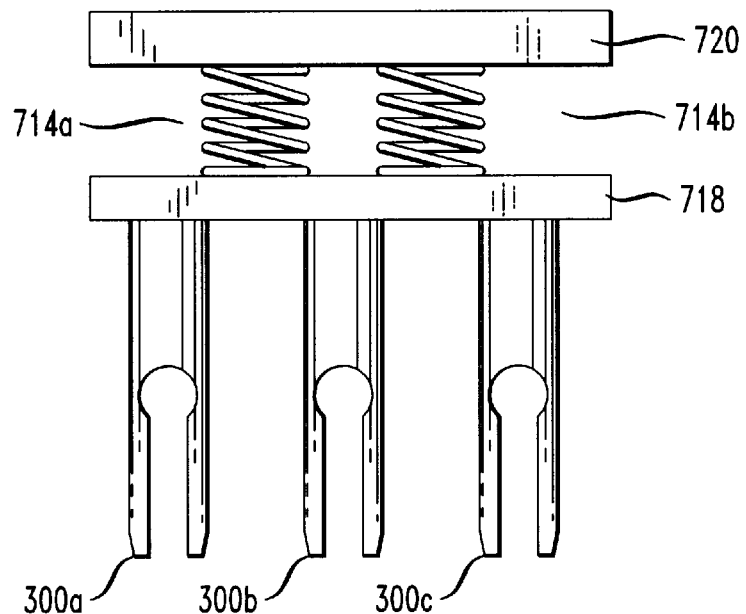
FIG. 7 shows a second exemplary embodiment of the micro volume liquid dispenser of FIG. 5.

In the illustrative embodiment shown in FIG. 7, the ability to selectivity discharge a select one or more fluid-dispensing members is forfeited if it is necessary to charge all fluid-dispensing members with liquid at the same time. If such selective discharge is not required, however, the embodiment shown in FIG. 7 offers a simpler configuration than, for example, the embodiment shown in FIG. 6. Of course, by filling only those fluid-dispensing members that are to be discharged in a selected time period, the ability to selectively discharge is retained.

Moreover, as previously noted, it should be understood that a wide variety of forces may be used to accelerate and/or decelerate fluid-dispensing members 200, 300 and 400. For example, depending upon the surface tension of the dispensable liquid, the force of gravity may impart sufficient acceleration to fluid dispensing members, in an appropriately configured micro volume fluid dispenser according to the present invention, to dislodge the fluid on abrupt deceleration. Further, pneumatic, hydraulic or electrodynamic-based actuators can be used to accelerate and/or decelerate fluid-dispensing members 200,300 and 400. Moreover, the operation of the present micro volume liquid dispenser can be automated, such as, for example, by using a microprocessor-based control system, as illustrated in FIG. 8.

Figure 8:
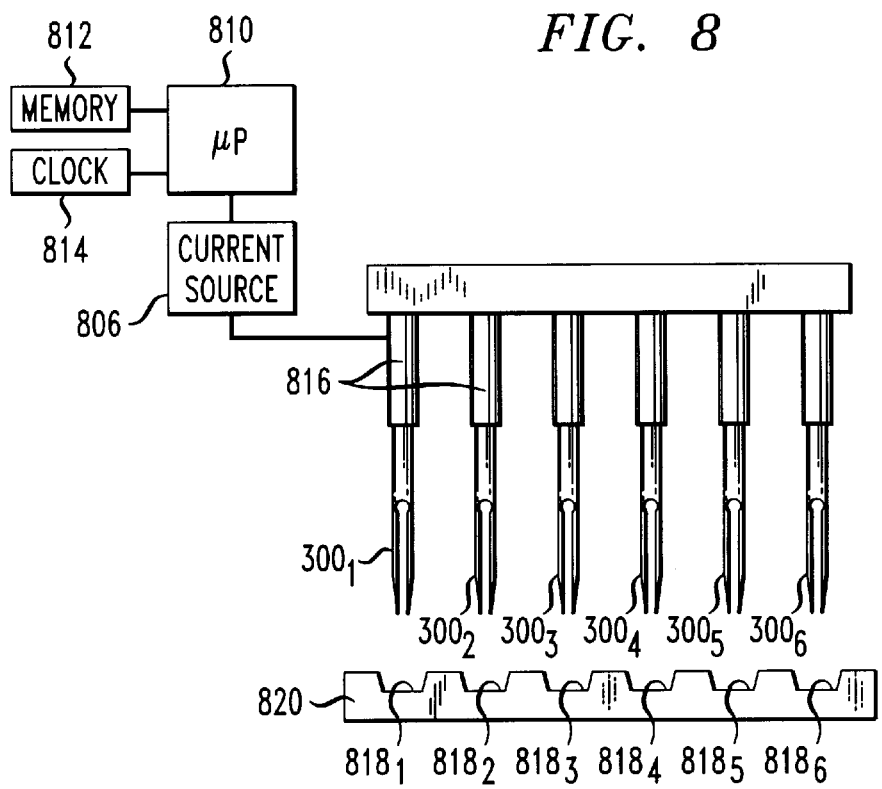
FIG. 8 shows a third exemplary embodiment of the micro volume liquid dispenser of FIG. 5 wherein operation of the dispenser is under microprocessor control.

In the illustrative embodiment depicted in FIG. 8, the actuator comprises solenoid 816. A solenoid, the structure and use of which is well known by those skilled in the electrical arts, typically includes a coil, an associated core, and linkage as appropriate to connect to a target presence. In the present context, the solenoid is in mechanical communication with a fluid-dispensing member $300_i$. In the illustrative embodiment shown in FIG. 8, a distinct solenoid 816 is provided for each fluid-dispensing member $300_i$, six of which are pictured. Each solenoid 816 is electrically connected to controllable current source 806 that is operable, in conjunction with other known processing electronics (not shown), to supply a current to a selected solenoid. The controllable current source 806 is under the control of a microprocessor 810, which is in communication with memory 812 and clock 814.

A dosing schedule is loaded into memory 812. The dosing schedule, which is accessed by the microprocessor 810, provides a time at which some or all fluid-dispensing members $300_i$, dispense their charge of liquid. An exemplary dosing schedule might dictate, for example, that fluid-dispensing members $300_1$–$300_3$ dispense their charge to a first group of segregated regions of a receiver, such as to respective wells $818_1$–$818_3$ of microtiter plate 820, at a first time. The schedule might further dictate that fluid-dispensing members $300_4$–$300_6$ dispense their charge of liquid to respective wells $818_4$–$818_6$ of microtiter plate 820 at a second time, and so forth.

At the scheduled time, microprocessor 810 sends a signal to controllable current source 806 directing it to apply a current to solenoids associated with the fluid-dispensing members $300_i$, that are scheduled to dispense. The current applied to the solenoids causes a core or rod located near the coil to accelerate rapidly into the coil. Fluid-dispensing member $300_i$, mechanically linked to the core, is likewise accelerated. Mechanical stops (not shown) are positioned as appropriate to rapidly decelerate the core and the interconnected fluid-dispensing member. Liquid retained in abruptly-decelerated fluid-dispensing members is discharged. The process may then be repeated for other fluid-dispensing members scheduled for dispensing at other times.

It will be appreciated that a variety of different control schemes, as will occur to those skilled in the art, can be used to automate operation of the present micro volume liquid dispenser. Moreover, it should be clear that any suitable number of liquid-dispensing members can be included in the present micro volume liquid dispenser. For example, a micro volume liquid dispenser having an array of ninety-six of such liquid dispensers would be advantageous for use with 96-well microtiter plates, such as are in common use in the pharmaceutical industry for conducting biological assays and the like.

Although specific embodiments of this invention have been shown and described herein, it is to be understood that these embodiments are merely illustrative of the many possible specific arrangements that can be devised in application of the principles of the invention. Numerous and varied other arrangements can be devised in accordance with these principles by those of ordinary skill in the art without departing from the scope and spirit of the invention.

I claim:

1. An article for dispensing a small volume of liquid, comprising:
   a fluid-dispensing member having two opposed surfaces in spaced relation to one another, the surfaces and space therebetween operable to generate a capillary effect;
   an actuator operable to accelerate and then abruptly decelerate the fluid-dispensing member, said abrupt deceleration causing liquid held between the two opposed surfaces to discharge therefrom; and
   a liquid director physically configured to substantially eliminate deviations in a path followed by said liquid discharged from the fluid-dispensing member.

2. The article of claim 1, wherein the fluid-dispensing member has a discontinuity in the spaced opposed surfaces and the space therebetween, said discontinuity operable to terminate the capillary effect.

3. The article of claim 2, wherein the discontinuity is a widening of the space between the opposed surfaces.

4. The article of claim 1, wherein the physical configuration of the liquid director is substantially needle-like, and wherein the liquid director is disposed within the space between the opposed surfaces and aligned along a centrally-located long axis of the fluid-dispensing member.

5. The article of claim 4, wherein the liquid director extends beyond opposed surfaces of the fluid-dispensing member along the direction of the long axis.

6. The article of claim 1, wherein the opposed surfaces are concave.

7. The article of claim 1, wherein the opposed surfaces are flat.

8. The article of claim 1, wherein the fluid-dispensing member further comprises an adjustment device operably connected to the two opposed surfaces, the adjustment device being operable to change the spacing between said two opposed surfaces.

9. The article of claim 8, wherein the adjustment device is a tightening screw.

10. The article of claim 1, wherein the actuator comprises a biasing member operable to store energy in a first position, wherein, when released from the first position, a portion of the stored energy is converted to kinetic energy thereby accelerating at least a part of the biasing member and also accelerating the fluid-dispensing member, which is in mechanical communication therewith.

11. The article of claim 10, wherein the biasing member is a spring.

12. The article of claim 1, wherein the actuator further comprises
   a first and a second stop, wherein the first stop is substantially nonmovable and the second stop is mechanically linked to the fluid-dispensing member and thereby accelerated therewith, and, wherein,
   the first stop is suitably positioned to engage the second stop after the second stop has moved a predetermined distance as a result of said acceleration, wherein,
   the fluid-dispensing member is abruptly decelerated when the first and second stops engage.

13. The article of claim 12, wherein the first stop is positioned to engage the second stop before substantially all stored energy available for conversion into kinetic energy is so converted.

14. The article of claim 1, further comprising an array of ninety-six fluid-dispensing members, wherein the ninety-six fluid-dispensing members are arranged so that when liquid in one of the fluid-dispensing members is dispensed, it is receivable by a complementary one of ninety-six wells arranged in an array on a suitably-positioned ninety-six well microtiter plate.

15. The article of claim 1, further comprising a microprocessor in communication with a memory and a clock, the microprocessor operable to actuate the actuator according to a dosing schedule.

16. The article of claim 15, wherein the microprocessor is in communication with a controllable current source, the controllable current source is in electrical communication with the actuator, and the actuator is a solenoid, wherein, the microprocessor is operable to send a signal to the controllable current source at a time dictated by the dosing schedule, which controllable current source is operable to apply a current to the solenoid, thereby actuating the solenoid and accelerating the fluid-dispensing member.

17. The article of claim 15, wherein the actuator is configured for one of either pneumatic, hydraulic or electrodynamic operation.

18. A micro volume liquid dispenser, comprising:

a fluid-dispensing member operable to generate a capillary effect;

a biasing element mechanically linked to the fluid-dispensing member, wherein said biasing element is operable to accelerate said fluid-dispensing member;

a first stop member depending from said fluid-dispensing member, wherein said first stop member is accelerated with said fluid-dispensing member, a second stop member that is substantially nonmovable and is aligned to engage the first stop member after said first stop member has been accelerated, and is further aligned to prevent said fluid-dispensing member from contacting a liquid receiving surface; and a liquid director physically configured to substantially eliminate deviations in a path followed by said liquid discharged from the fluid-dispensing member.

19. The micro volume liquid dispenser of claim 18, wherein said fluid dispensing member comprises two opposed surfaces in spaced relation to one another, wherein there is a discontinuity in the spaced opposed surfaces and the space therebetween, said discontinuity operable to terminate said capillary effect.

20. A method for discharging a small volume of liquid, comprising:

accelerating a liquid carrier operable to retain liquid via a capillary effect; abruptly decelerating the liquid carrier while preventing it from contacting a surface of a receiver; and directing said liquid along a liquid director that extends beyond said liquid carrier towards said receiver.

21. The method of claim 20, wherein the step of accelerating further comprises converting the stored energy within a biasing element to kinetic energy that is imparted to the liquid carrier.

22. An article for dispensing a small volume of liquid, comprising:

a fluid-dispensing member having two opposed surfaces in spaced relation to one another, the surfaces and space therebetween operable to generate a capillary effect;

an actuator operable to accelerate and then abruptly decelerate the fluid-dispensing member, said abrupt deceleration causing liquid held between the two opposed surfaces to discharge therefrom; and a tightening screw operably connected to the two opposed surfaces, the tightening screw operable to change the space between said two opposed surfaces.

23. The article of claim 22, wherein said fluid-dispensing member has a liquid director physically configured to substantially eliminate deviations in a path followed by said liquid discharged from the fluid-dispensing member.

24. An article for dispensing a small volume of liquid, comprising:

a fluid-dispensing member operable to generate a capillary effect;

means for accelerating said fluid-dispensing member;

means for rapidly decelerating said fluid dispensing member;

means for preventing said fluid-dispensing member from contacting a receiver that receives liquid dispensed from said fluid-dispensing member upon said rapid deceleration; and means for substantially eliminating deviations in a path followed by said liquid dispensed from said fluid-dispensing member.

25. The article of claim 24, wherein said fluid-dispensing member comprises two spaced opposed surfaces.

26. The article of claim 25, further comprising:

means for adjusting a space between said two spaced opposed surfaces.

* * * * *